United States Patent [19]
O'Leary et al.

[11] Patent Number: 5,118,512
[45] Date of Patent: Jun. 2, 1992

[54] PROCESS FOR CRYOPRESERVING BIOLOGICAL MATERIALS AND MATERIALS PREPARED THEREBY

[75] Inventors: Robert K. O'Leary, Spring Lake; Ann Prewett, Fairhaven, both of N.J.

[73] Assignee: Osteotech, Inc. (a Delaware Corp.), Shrewsbury, N.J.

[21] Appl. No.: 468,709

[22] Filed: Jan. 23, 1990

[51] Int. Cl.⁵ .................... A61K 35/32; A01N 1/02
[52] U.S. Cl. .................... 424/549; 424/520; 424/548; 435/1; 435/240.1
[58] Field of Search ............... 435/1, 240.1; 424/549, 424/520, 548

[56] References Cited

U.S. PATENT DOCUMENTS 4,559,298 12/1985 Fahy ........................................ 435/1

OTHER PUBLICATIONS

Dil 'barkhanov et al.—Chem. Abst., vol. 93 (1980) p. 137936Z.
Williams et al.—Chem. Abst., vol. 89 (1978) p. 645b.

Primary Examiner—Sam Rosen
Attorney, Agent, or Firm—Elliot M. Olstein; Raymond J. Lillie

[57] ABSTRACT

A process for cryopreserving a biological material which comprises contacting the biological material with both an effective amount at least one cryopreservation agent, and an agent to increase diffusion of the cryopreservation agent into the biological material, such as a surfactant or a permeation enhancer.

11 Claims, No Drawings

PROCESS FOR CRYOPRESERVING BIOLOGICAL MATERIALS AND MATERIALS PREPARED THEREBY

This invention relates to the processing of biological materials, such as allograft tissue for use in grafts and transplants, hybridomas, myelomas, permanent cell lines, primary culture cell lines, transformed cell lines, and genetically engineered cells. More particularly, this invention relates to a process for cryopreserving a biolgoical material wherein the tissue is contacted with a cryopreservation agent, whereby there is improved penetration and diffusion of the cryopreservation agent into the biological material.

In general, in processing allograft tissue for use in grafts and transplants, the allograft tissue may include, for example, musculoskeletal tissue such as bone, cartilage, and connective tissue such as fascia, menisci, tendons, ligaments, etc. Allograft tissue also may include other tissues such as dura mater, tympanic membranes, skin and corneal tissue. The tissue is removed from the body under sterile conditions. The tissue is then soaked in an antibiotic and then wrapped under sterile conditions for transport to facilities for further processing.

Once the tissue is ready to be processed further, it is unwrapped under sterile conditions and, in the case of bone, then debrided; i.e., connective tissue and periosteum are removed from the bone. After debridement, the bone is shaped under sterile conditions into a specific size meeting formal specifications for surgical requirements.

Such freezing, or cryopreservation, is carried out by treating the allograft tissue with a cryopreservation medium including at least one cryopreservation agent. After the allograft tissue is treated with the at least one cryopreservation agent, the tissue is frozen in a conventional freezing apparatus. The tissue may be placed in a cryotube or in a protective wrap, such as a protective foil, at an initial temperature of, for example, about 20° C. The cryotube or wrap containing the tissue is then placed in a freezer, wherein the temperature is decreased at a controlled rate (e.g., about 1° C./min.) until the temperature has been lowered to a desired cryopreservation temperature (e.g., between about $-100°$ C. and $-70°$ C.) and/or the cryotube or protective wrap containing the tissue may be placed in liquid nitrogen, which may be at a temperature of $-196°$ C. The cryopreservation agent aids in protecting the allograft tissue cells by preventing lysis of such cells. In this manner, the allograft tissue may be preserved for extended periods of time.

Cells may be cryopreserved by suspending the cells in a cryopreservation medium including at least one cryopreservation agent. The suspension is contained in a cryotube or other type of container designed to withstand cryopreservation temperatures. As an example of the cryopreservation of a cell suspension, the suspension may be placed in a freezer whereby freezing takes place at a controlled rate (e.g., from about 1° C. to about 5° C./min.) until the suspension is at a desired cryopreservation temperature (e.g., about $-70°$ C.). The suspension may be frozen as such overnight, and then the container holding the suspension may be placed in a liquid nitrogen bath at a temperature of $-196°$ C. Cells which may be cryopreserved include myeloma cells, hybridomas, permanent cell lines, primary cell lines, transformed cell lines, genetically engineered cells, red blood cells, platelets and bone marrow cells.

It is an object of the present invention to provide a process whereby there is achieved improved penetration, diffusion, permeation, solubility, and sorption of a cryopreservation agent into biological materials.

In accordance with an aspect of the present invention, there is provided a process for cryopreserving a biological material which comprises contacting the biological material with both an effective amount of at least one cryopreservation agent and an agent to increase diffusion of the at least one cryopreservation agent into the biological material, which agent is preferably a surfactant or a permeation enhancer.

The term "to increase diffusion", as used herein, means that the agent which increases diffusion of the cryopreservation agent into the biological material, may increase the total amount of cryopreservation agent which diffuses through the biological material and/or increase the rate of diffusion of the cryopreservation agent through the biological material.

Cryopreservation agents which may be employed include, but are not limited to dimethyl sulfoxide, glycerol, liquid carbon dioxide, fish blood glycoproteins isolated from species such as species of the genus Trematomus and Borchgrebinki arachis, formamide, polyvinyl pyrrolidone and hydroxyethyl starch. One or a combination of these cryopreservation agents may be employed within the scope of the present invention. It is also contemplated that a protein (e.g., a serum, such as fetal calf serum), may be employed along with one or a combination of cryopreservation agents as part of a cryopreservation medium.

The agent for increasing diffusion of the cryopreservation agent into the biological material is preferably a surfactant or a permeation enhancer. The surfactant employed in accordance with the present invention may be a cationic, non-ionic, anionic, or amphoteric surfactant. The surfactant should be a biocompatible surfactant and miscible with the cryopreservation agent.

Cationic surfactants which may be employed include quaternary amino or nitrogen compounds; quaternary ammonium salts such as benzalkonium chloride, alkyltrimethylammonium salts, and alkylpyridinium salts; aliphatic mono-, di-, and polyamines; rosin-derived amines; amine oxides, such as polyoxyethylene alkyl and alicyclic amines, N, N, N, N tetrakis-substituted ethylene diamines, amide-linked amines, preferably those prepared by the condensation of a carboxylic acid with a di-or polyamine, and sodium tauro-24, 25-dihydrofusidate.

Anionic surfactants which may be employed include sulfates such as alkyl sulfates (for example, sodium dodecyl sulfate), sulfated fats and oils, sulfated oleic acid, sulfated alkanolamides, sulfated esters, and alcohol sulfates; sulfonates such as alkylaryl sulfonates, olefin sulfonates, ethoxylated alcohol sulfates, and sulfonates of ethoxylated alkyl phenols; sulfates of fatty esters; sulfates and sulfonates of alkyl phenols; lignosulfonates; sulfonates of condensed naphthalenes; sulfonates of naphthalene; dialkyl sulfosuccinates, preferably sodium derivatives; sodium derivatives of sulfo-succinates, such as the disodium ethoxylated nonyl phenol half ester of sulfosuccinic acid, the disodium ethoxylated alcohol ($C_{10}$–$C_{11}$), half-ester of sulfosuccinic acids, etc., petroleum sulfonates, such as alkali salts of petroleum sulfonates; for example, sodium petroleum sulfonate (Acto 632); phosphate esters, such as alkali phosphate esters, and a potassium salt of phosphate ester (Triton H66); sulfonated alkyl esters (for example, Triton GR 7); carboxylates, such as those of the formula (RCOO-)—(M)+ wherein R is an alkyl group having from 9-21 carbon atoms, and M is a metal or an amine; and sodium polymeric carboxylic acid (Tamol 731) and the like.

Nonionic surfactants which may be employed include polyoxyethylenes; ethoxylated alkyl phenols, ethoxylated alipatic alcohols; carboxylic acid esters, such as glycerol esters, polyethylene glycol esters, and polyoxyethylene fatty acid esters; anhydrosorbitol esters and ethoxylated anhydrosorbitol esters; glycol esters of fatty acids; ethoxylated natural fats, oils, and waxes; carboxylic amides, such as diethanolamine condensates, and monoalkanolamine condensates; polyoxyethylene fatty acid amides; polyalkylene oxide block copolymers, preferably polyethylene and polypropylene oxide block copolymers; and polysiloxane-polyoxyalkylene copolymers; 1-dodecylazacycloheptan-2-one (Nelson R & D); polyethylene glycol monolaurate (Alza); and Macrochem's SEPA nonionic surfactant.

Preferred non-ionic surfactants are non-ionic surfactants which are ethylene oxide condensation products (polyoxyethylene) containing more than two, and preferably at least five ethylene oxide groups, with at least one end group thereof being terminated by condensation with either an alcohol, alkylphenol, or a long chain fatty acid. A particularly preferred non-ionic surfactant is an octylphenoxy polyethoxyethanol surfactant known as Triton X-100.

Amphoteric surfactants include N-coco-3 aminopropionic acid and its sodium salt; disodium salts of N-tallow-3-iminodipropionate and N-lauryl-3-iminodipropionate; N-carboxymethyl-N cocoalkyl-N-dimethylammonium hydroxide; N-carboxymethyl-N-dimethyl-N-(9-octadecenyl) ammonium hydroxide; (1-carboxy heptadecyl) trimethylammonium hydroxide; (1-carboxyundecyl) trimethylammonium hydroxide; sodium salts of N-cocoamidoethyl-N-hydroxyethylglycine and N-hydroxyethyl-N-stearamido-glycine; sodium salts of N-hydroxyethyl-N-lauramido-B-alanine and N-cocoamido-N-hydroxyethyl-B-alanine; sodium salts of mixed alicyilic amines, ethoxylated and sulfated sodium salts or free acids of 2-alkyl-1 carboxymethyl-1-hydroxyethyl-2-imidazolinium hydroxide; the disodium salt of 1, 1-bis (carboxymethyl)-2-undecyl-2-imidazolinium hydroxide; and the sodium salt of a propoxylated and sulfated oleic acid-ethylenediamine condensate.

In lieu of a surfactant, it is to be understood that a permeation enhancer may be employed as the agent to increase diffusion of the at least one cryoprservation agent into the biological material. The term "permeation enhancer" as used in the art and herein means an agent which aids or assists a material (e.g., a cryopreservation agent or a drug) to dissolve into and diffuse through the skin. Applicants have found that such permeation enhancers may be employed to increase diffusion of a cryopreservation agent into a biological material.

Permeation enhancers which may be employed within the scope of the present invention include glycerol monolaurate; hexamethylene lauramide; dimethyl formamide; propylene glycol; diethyltoluamide; N-methyl-2-pyrrolidone; decylmethylsulfoxide; benzyl alcohol; dimethyl sulfoxide; alkyl-N-N-dialkyl-substituted amino acetates; lecithin; dimethylacetamide; laurocapram; dodecyl-L-pyroglutamate; 1-oxohydrocarbyl-substituted azacyclohexanes; azone; hydroxyethyl acetamide; tetrahydrofurfuryl alcohol; methyl laurate; isopropyl palmitate; isopropyl myristate; and isopropyl stearate. Preferred permeation enhancers are isopropyl palmitate and isopropyl myristate. It is to be understood, however, that the scope of the present invention is not to be limited to the specific permeation enhancers hereinabove described.

The cryopreservation agent is employed alone or in an aqueous solution. Preferably, the cryopreservation agent is added in an aqueous solution in an amount of from about 1% to about 25%. The agent to increase diffusion of the cryopreservation agent into the tissue, such as a surfactant or permeation enhancer, is added in an amount effective to increase diffusion of the cryopreservation agent into the tissue. The agent is preferably added to an aqueous solution of the cryopreservation agent in an amount of from about 0.0001% to about 10% of the resulting aqueous solution, preferably from about 0.01% to about 10%. The combination of cryopreservation agent and surfactant or permeation enhancer is preferably applied to the tissue as an aqueous mixture. In one alternative, the cryopreservation agent and surfactant or permeation enhancer may be contained within unilamellar or multilamellar liposomes, which are suspended in a liquid medium. The liposomes may be broken after the liquid medium is contacted with the biological material, whereby the cryopreservation agent and the agent to increase diffusion of the cryopreservation agent into the biological material are delivered to the biological material. Alternatively, the liposomes may attach to a receptor on the cells, whereby the cells take up the liposomes and their contents by pinocytosis.

Although the present invention is not intended to be limited to any theoretical reasoning, it is believed that, when a surfactant is employed as the agent to increase diffusion of the cryopreservation agent into the biological material, the combination of cryopreservation agent and surfactant alters the surface tension of the cells of the biological material, thereby providing for improved or enhanced penetration of the cryopreservation agent into and diffusion of the cryopreservation agent through the biological material. The improved absorption of the cryopreservation agent into the biological material provides for enhanced ability of the cryopreservation agent to protect the biological material as the biological material is preserved for an extended period of time. In addition, the use of a surfactant can provide viricidal activity in that surfactants can function to disrupt viruses.

When a permeation enhancer is employed as the agent to increase diffusion of the cryopreservation agent into the biological material, it is believed that the permeation enhancer increases the solubility of the cryopreservation agent; i.e., the permeation enhancer increases the ability of the cryopreservation agent to dissolve into the biological material. It is also believed that the permeation enhancer increases the diffusion, or rate of movement, of the cryopreservation agent through the biological material.

Biological materials which may be preserved in accordance with the present invention include, but are not limited to, allograft tissue, myeloma cells, hybridoma cells, permanent and transformed cell lines, such as Hep62 hepatocarcinoma and Ros172 osteosarcoma, primary culture cell lines, such as chicken embryo fibrobalst cells, genetically engineered cell lines, HeLa cells, Chinese hamster ovary (CHO) cells, red blood cells, platelets, and bone marrow cells.

Allograft tissue which may be cryopreserved in accordance with the present invention includes bone tissue, cartilage, and connective tissue such as tendons, fascia, menisci, and ligaments. Specific examples of musculoskeletal tissue which may be prepared for use in grafts or transplants in accordance with the present invention include cortical/cancellous tissue, cancellous chips, cloward dowels, iliac crest wedges, ilium bicortical strips, ilium tricortical strips, cortical strips, bone-tendon-bone (patellar) grafts, achilles tendon (which may also include a calcaneous), fascia lata, proximal tibia, distal femur, proximal humerus, (with or without rotator cuff), proximal femur, whole knee, whole femur, fibula, ribs, femoral heads, fibular shafts, femoral shafts, and tibial shafts.

It is also contemplated within the scope of the present invention that allograft tissue other than musculoskeletal tissue, such as dura mater, tympanic membranes, skin and corneal tissue, may be cryopreserved as well.

In accordance with another aspect of the present invention, there is provided a product comprising a biological material prepared by the process hereinabove described.

It is to be understood, however, that the scope of the present invention is not to be limited to the specific embodiments described above. The invention may be practiced other than as particularly described and still be within the scope of the accompanying claims.

What is claimed is:

1. A process for cryopreserving bone, comprising: contacting bone with both an effective amount of at least one cryopreservation agent, and an agent to increase diffusion of the at least one cryopreservation agent into the bone and then freezing said bone.

2. The process of claim 1 wherein the cryopreservation agent is selected from the class consisting of dimethyl sulfoxide, glycerol, liquid carbon dioxide, fish blood glycoproteins isolated from species of the genus Trematomus or Borchgrebinki arachis, formamide, polyvinyl pyrrolidone, and hydroxyethyl starch.

3. The process of claim 1 wherein said agent to increase diffusion of the cryopreservation agent into the bone is a surfactant.

4. The process of claim 3 wherein the surfactant is a nonionic surfactant.

5. The process of claim 1 wherein said agent to increase diffusion of the cryopreservation agent into the bone is a permeation enhancer.

6. The process of claim 3 wherein the surfactant is miscible with said at least one cryopreservation agent.

7. The process of claim 1 wherein said at least one cryopreservation agent and said agent to increase diffusion of the cryopreservation agent into the bone are applied as an aqueous mixture.

8. The process of claim 1 wherein said at least one cryopreservation agent is added in an aqueous solution in an amount of from about 1% to about 25%.

9. The process of claim 1 wherein the agent to increase diffusion of the cryopreservation agent into the bone is added in an aqueous solution in an amount of from about 0.0001% to about 10%.

10. A product comprising a bone prepared by the process of claim 1.

11. The process of claim 4 wherein said non-ionic surfactant is an octylphenoxy polyethoxyethanol surfactant.

* * * * *